United States Patent [19]

Maziere et al.

[11] Patent Number: 5,242,678

[45] Date of Patent: Sep. 7, 1993

[54] BR*-DIAGNOSTICS FOR MONOAMINE RECEPTORS

[75] Inventors: Bernard Maziere, Gif-sur-Yvette, France; Helmut Wachtel, Berlin, Fed. Rep. of Germany; Peter-Andreas Loeschmann, Berlin, Fed. Rep. of Germany; Rainer Dorow, Berlin, Fed. Rep. of Germany; Bernard Acksteiner, Berlin, Fed. Rep. of Germany; Dominique Comar; Christian Loch, both of Paris, France

[73] Assignee: Schering Aktiengesellschaft, Berlin, Fed. Rep. of Germany

[21] Appl. No.: 371,134

[22] Filed: Jun. 26, 1989

Related U.S. Application Data

[62] Division of Ser. No. 72,090, Jul. 10, 1987, Pat. No. 4,857,298.

[30] Foreign Application Priority Data

Jul. 10, 1986 [DE] Fed. Rep. of Germany ....... 3623437

[51] Int. Cl.$^5$ .................... A61K 43/00; C07D 457/04; C12Q 1/00
[52] U.S. Cl. ........................................ 424/1.1; 424/9; 546/68; 435/7.21
[58] Field of Search ....................... 424/1.1, 9; 546/68, 546/67; 435/7.21

[56] References Cited

U.S. PATENT DOCUMENTS

| | | |
|---|---|---|
| 3,920,664 | 11/1975 | Clemens et al. |
| 3,959,288 | 5/1976 | Bach et al. |
| 4,054,660 | 10/1977 | Clemens et al. |
| 4,199,579 | 4/1980 | Ferrari et al. |
| 4,299,836 | 11/1981 | Mago nee Karacsony et al. |
| 4,417,051 | 11/1983 | Sauer. |
| 4,695,635 | 9/1987 | Sauer et al. |
| 5,158,957 | 10/1992 | Brumby et al. ............. 514/288 |

FOREIGN PATENT DOCUMENTS

| | | |
|---|---|---|
| 0056358 | 7/1982 | European Pat. Off. |
| 3247514 | 6/1984 | Fed. Rep. of Germany. |

OTHER PUBLICATIONS

Maziere et al., "$^{76}$Br Bromolisuride: A New Radiopharmacentical for in Vivo Studies", J. Biophys Biom (Sep. 15, 1986), 10 (2 Supp), p. 25.6 (CA 106:1536a).

Maziere et al., "In Vivo Quantitative Imaging of Dopamine Receptors in Human Brain Using Positron Emission Tomography and $^{76}$Br Bromospiperone," European Journal of Pharmacology, 114, pp. 267-272 (1985).

Maziere et al., "$^{76}$Br Bromolisuride: A New Tool for Quantitative In Vivo Imaging of D-2 Dopamine Receptors," European Journal of Pharmacology, 127, pp. 239-247 (1986).

Maziere et al., "$^{76}$Br-Bromospiroperidol: A New Tool for Quantitative In Vivo Imaging of Neuroleptic Receptors," Life Sciences, vol. 35, pp. 1349-1356 (1984).

Kung et al., "Synthesis and Biodistributionof Neutral Lipid-Soluble Tc-99m Complexes that Cross the Blood-Brain Barrier," J. Nucl. Med. 25:326-332 (1984).

Kung et al., "Synthesis of New Bis (aminoethanethiol) (BAT) Derivatives: Possible Ligands for $^{99m}$Tc Braim Imaging Agents," Journal of Medicinal Chemistry, 28, 1280-1284 (1985).

Phelps et al., "Positron Emission Tomography: Human Brain Function and Biochemistry", Science, vol. 228, No 4701, pp. 799-809 (May 17, 1985).

Primary Examiner—Robert L. Stoll
Assistant Examiner—Matthew Zmurko
Attorney, Agent, or Firm—Millen, White, Zelano, & Branigan

[57] ABSTRACT

Compounds of general Formula I labeled with $^{75}$Br, $^{76}$Br, $^{77}$Br, $^{80m}$Br or $^{80}$Br isotopes wherein
R$^6$ is a C$_{1-6}$ hydrocarbon residue and C$_2$- - -C$_3$, C$_9$- - -C$_{10}$ is a single or a double bond, as well as their acid addition salts, as diagnostic media to image dopamine.

19 Claims, No Drawings

BR*-DIAGNOSTICS FOR MONOAMINE RECEPTORS

This is a division of U.S. Ser. No. 07/072,090, filed Jul. 10, 1987, now U.S. Pat. No. 4,857,298.

CROSS-REFERENCE TO RELATED APPLICATION

This application is related to appln. Ser. No. 07/072,090, now U.S. Pat. No. 4,857,298 issued Aug. 15, 1989, which disclosure is incorporated by reference herein.

BACKGROUND OF THE INVENTION

This invention relates to ergolinylurea derivatives containing radioactive bromine, their preparation, and their use as diagnostic agents.

SUMMARY OF THE INVENTION

It is an object of this invention to provide new compounds valuable as diagnostics.

Upon further study of the specification and appended claims, further objects and advantages of this invention will become apparent to those skilled in the art.

These objects have been achieved by providing new compounds of Formula I

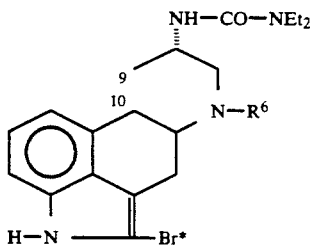

wherein $R^6$ is a $C_{1-6}$ hydrocarbon residue and $C_9$---$C_{10}$ is a single or double bond, as well as their acid addition salts.

Suitable hydrocarbon residues $R^6$ include straight chained, branched, saturated, unsaturated, acyclic or cycloaliphatic groups of up to 6 carbon atoms. Hydrocarbon residues of 1-4 carbon atoms are preferred, for example, methyl ethyl, n-propyl, isopropyl, a butyl, cyclopropylmethyl, 2-propenyl, allyl, etc. Thus, generally suitable groups are aklyl, alkenyl, alkynyl, each of these groups optionally substituted by a cycloalkyl group, or cycloalkyl, cycloalkenyl, cycloalkynyl, etc.

Suitable radioactive bromine isotopes Br* are, for example the $^{75}Br$, $^{76}Br$, $^{77}Br$, $^{80m}Br$ and $^{80}Br$ isotopes.

Autoradiography and, in particular, positron emission tomography (PET) and single-photon emission computer tomography (SPECT) are suitable for the detection of functional and structural cerebral changes. Since cerebral functions are organized topographically, and no conclusion can be drawn from the functional condition of a cell or a united cell structure—as, for example, in case of the liver—with respect to the function of the entire organ, visualization and quantification of the spatial and chronological distribution of morphological and functional tissue parameters represent an improvement in diagnostics.

It is known that ergolinylurea derivatives affect noradrenergic, dopaminergic and serotoninergic neurons; by binding to the presynaptic or postsynaptic neuronal receptors, the activity of the natural neurotransmitter is imitated (agonist) or the activity of the natural neurotransmitter is counteracted (antagonist). It is furthermore known that imaging of dopamine receptors is possible by PET using dopamine antagonists that emit positrons (Maziere, B., et al., Life Sci. 35:1349, 1984).

It has now been discovered that the compounds of this invention, on account of their affinity to monoamine receptors, are especially well suited for diagnostic purposes. They can be utilized for the in vivo and in vitro imaging of dopaminergic and other monoaminergic systems and thus are suitable for the visualization of structure and function of dopaminergic and other monoaminergic systems in organisms or parts thereof, such as, for example, the entire brain, basal ganglia, frontal brain, etc.

Diagnostically, recognition of early or advanced cases of Parkinson's disease is possible from an observed lesser enrichment, as compared to a conventional standard, of the labeled dopamine receptor antagonists, such as, for example, radioactively labeled 2-bromolisuride, in the basal ganglia; by previous administration of D-2-antagonists, image representation is prevented, showing the efficiency of this invention in imaging central dopamine receptors. Since there is no binding to serotonin receptors, and enrichment takes place within a very brief time period so that radiation stress is low, the compounds of this invention, particularly radioactively labeled 2-Br* lisuride, are especially suitable for the selective imaging of central dopamine receptors.

However, it is likewise possible to identify disorders due to lack of dopamine, or disturbances of the dopamine system, such as, for example, in case of senile dementia, motor hypo-, dys-, or hyperfunction, including late consequences of medicament ingestion, again by reference to a standard image. Furthermore, it is also possible to differentiate, with respect to forms and symptoms, disturbances of the limbic and cortical dopaminergic systems. This is especially valuable, for example, in the field of psychoses and especially in schizophrenias, thus making them accessible to differentiated therapy and therapy control. Dopamine receptors are also found in the hypophysis so that imaging of prolactinomas and their metastases is also possible. The compounds of this invention thus can likewise be employed for the imaging, detection and diagnosis of tumors and metastases.

Thus, the compounds of this invention can be used in a method for imaging dopamine receptors, e.g., using one of the conventional methods mentioned above, typically to determine the level of natural dopamine neurotransmitter function, inter alia. The method can be carried out analogously to the known method with other agents, e.g., as disclosed in Phelps, M. E., Mazziotta, J. C., Science 228, No. 4701: 799–809, 1985 and Maziere, B., et al, Europ. J. of Pharmocol 114: 267–272, 1985. Typically, the compounds are administered parenterally (but also possibly enterally) in the form of their water soluble salts or in a conventional buffer solution. The mixture administered contains the compounds typically in a concentration of 0.01-2 nmoles/ml. Typical dosages are 0.01-10 μg/kg administered 5-15 minutes prior to the first imaging step.

Suitable formulations are those known for the underlying therapeutic agents per se. See, e.g., ethanol-propanediol-saline or ethanol-saline, after sterile filtration of the HPLC-separated compound.

A further advantage of the compounds of this invention is that labeling is effected on known therapeutics by substitution on them with radioactive bromine, thus obtaining in very good yields compounds having a very high specific activity, these compounds likewise being known as therapeutics in the unlabeled condition.

The compounds of this invention can be prepared by reacting the corresponding compound of general Formula I which is not brominated in the 2-position, in the presence of an oxidizing agent with Na-[$^{75}$Br, $^{76}$Br, $^{77}$Br, $^{80m}$Br or $^{80}$Br] bromide*.

For example, the compounds of general Formula I can be produced by reacting the unbrominated compounds with radioactively labeled sodium-[Br*] bromide in the presence of an oxidizing agent. Suitable oxidizing agents are, for example, chloramine-T, $H_2O_2$/glacial acetic acid, and others. The reaction is performed at room temperature within 1–30 minutes in aprotic or protic solvents, such as, for example, chlorinated hydrocarbons, such as dichloromethane, dichloroethane, chloroform, or lower aliphatic carboxylic acids, such as acetic acid, propionic acid, etc. The substitution typically takes 15–60 minutes.

The reaction can be conducted under an inert gas, such as, for example, nitrogen or argon.

The compounds are purified by the usual methods, for example by HPL chromatography.

The starting compounds are known, for example, from EP-21206. The physiologically compatible acid addition salts can be conventionally obtained from the corresponding acids, for example, according to the processes described in EP-A-220 129 using inorganic acids, e.g., hydrochloric acid, nitric acid, phosphoric acid, sulfuric acid, hydrobromic acid, hydriodic acid, nitrous acid or phosphorous acid, or organic acids, such as, for example, aliphatic mono- or dicarboxylic acids, phenyl-substituted alkane-carboxylic acids, hydroxyalkanecarboxylic acids, or alkenedicarboxylic-acids, aromatic acids or aliphatic or aromatic sulfonic acids. Physiologically acceptable salts of these acids are, therefore, e.g., sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caproate, heptanoate, propiolate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluene-sulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate or naphthalene-2-sulfonate.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLE 1

0.01 umol of lisuride is suspended in 200 ul of acetic acid; 1,850–3,700 MBq of Na$^{76}$Br (aqueous solution) and an oxidizing solution (200 ul) made up of 30% $H_2O_2$/glacial acetic acid (2:1) are added thereto. The mixture is allowed to react for three minutes and separation is performed over a semi-preparative HPLC column, thus obtaining 2-[$^{76}$Br]-bromolisuride.

Analogously, the correspondingly labeled compounds are obtained with $^{75}$Br, $^{76}$Br, $^{77}$Br, $^{80m}$Br and $^{80}$Br.

EXAMPLE 2

Preparation of a Solution 0.01 μmol of a purified compound of this invention is dissolved in 5 ml of ethanol-propanediol-saline (2/6/92) solution.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A labeled radioactive bromine compound of Formula I

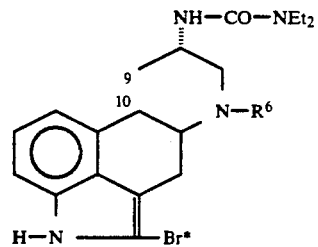

wherein
R$^6$ is a C$_{1-6}$ aliphatic hydrocarbon residue and C$_9$---C$_{10}$ is a single or a double bond, or a pharmaceutically acceptable acid addition salt thereof.

2. A compound of claim 1, wherein Br* is $^{75}$Br, $^{76}$Br, $^{77}$Br, $^{80m}$Br or $^{80}$Br.

3. A compound of claim 1, wherein Br* is $^{76}$Br.

4. A compound of claim 1, wherein C$_9$---C$_{10}$ is a single bond.

5. A compound of claim 1, wherein C$_9$---C$_{10}$ is a double bond.

6. A compound of claim 1, wherein R$^6$ is alkyl.

7. A compound of claim 1, wherein R$^6$ is methyl.

8. 2-Br*-lisuride, a compound of claim 1.

9. A compound of claim 8, wherein Br* is $^{75}$Br, $^{76}$Br, $^{77}$Br, $^{80m}$Br or $^{80}$Br.

10. 2-$^{76}$Br-lisuride, a compound of claim 1.

11. A method of imaging monoamine receptors in tissue in vitro comprising contacting the tissue with a compound of claim 1 and subjecting the resultant tissue to a radioactive-bromine-sensitive imaging measurement.

12. A method of imaging monoamine receptors in tissue in vitro comprising contacting the tissue with a compound of claim 8 and subjecting the resultant tissue to a radioactive-bromine-sensitive imaging measurement.

13. A method of claim 11, wherein said measurement is PET or SPECT.

14. A method of imaging monoamine receptors in a patient comprising administering to the patient a compound of claim 1 in a manner and amount effective to bind said dopamine receptors and subjecting the patient to a radioactive-bromine-sensitive imaging measurement.

15. A method of imaging monoamine receptors in a patient comprising administering to the patient a compound of claim 8 in a manner and amount effective to bind said dopamine receptors and subjecting the patient to a radioactive-bromine-sensitive imaging measurement.

16. A method of claim 14, wherein said measurement is PET or SPECT.

17. A method of imaging monoamine receptors in a patient comprising subjecting the patient to a radioactive-bromine-sensitive imaging measurement, said patient having been administered a compound of claim 1 in a manner and amount effective to bind said dopamine receptors.

18. A method of claim 11, wherein said receptors are dopamine receptors.

19. A method of claim 16, wherein said receptors are dopamine receptors.

* * * * *